United States Patent [19]
Meers et al.

[11] Patent Number: 6,120,797
[45] Date of Patent: *Sep. 19, 2000

[54] N-ACYL PHOSPHATIDYLETHANOLAMINE-MEDIATED LIPOSOMAL DRUG DELIVERY

[75] Inventors: Paul R. Meers, Princeton Junction; Tong Shangguan, Princeton; Shaukat Ali, Monmouth Junction, all of N.J.; Andrew Janoff, Yardley, Pa.; Charles Pak, Plainsboro, N.J.

[73] Assignee: The Liposome Company, Inc., Princeton, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/951,056

[22] Filed: Oct. 15, 1997

Related U.S. Application Data

[60] Provisional application No. 60/028,557, Oct. 15, 1996.

[51] Int. Cl.$^7$ ..................................................... A61K 9/127
[52] U.S. Cl. .......................... 424/450; 436/829; 935/54; 428/402.2
[58] Field of Search .................................. 424/450, 1.21, 424/9.321, 9.51, 417; 436/829; 935/54; 428/402.2

[56] References Cited

PUBLICATIONS

Akoka, et al., "A phosphorus magnetic resonance spectroscopy and a differential scanning calorimetry study of the physical properties of N–acylphophatidylethanolamines in aqueous dispersions," (1988) Chem. Phys. Lipids 46, 43–50.

Bangham, et al., Diffusion of Univalent Ions across the Lamellae of Swollen Phospholipids, J. Miol. Biol. (1965), 13, 238–252.

Batzri, et al., "Single bilayer liposomes prepared without sonication", BBA, 298 (1973), 1015–1019.

Cullis, P. R., et al., "Lipid Polymorphism and the Functional Roles of Lipids in Biological Membranes" (1979) Biochim. Biophys. Acta 559, 399–420.

Deamer, et al., *Liposomes*, "Liposome Preparation: Methods and Mechanisms", M. Ostro, ed., Marcel Dekker, Inc. New York (1983), Chapter 1, pp., 27–51.

Domingo, et al, "The influence of N–acyl chain length of the phase behaviour of natural and synthetic N–acylethanolamine phospholipids", Chemistry and Physics of Lipids, 75 (1995) 15–25.

Domingo, et al., "Role of headgroup structure in the phase behavior of N–acylethanolamine phospholipids: hydrogen–bonding ability and headgroup size," 1994, Chemistry and Physics of Lipids, 69, 229–240.

Domingo, et al., "Incorporation of N–acylethanolamine phospholipids into egg phosphatidylcholine vesicles: characterization and permeability properties of the binary systems," (1993) Biochim. Biophys. Acta 1148, 308–316.

Ellens, et al., "Membrane Fusion and Inverted Phases," (1989) Biochemistry 28, 3692–3703.

(List continued on next page.)

*Primary Examiner*—Gollamudi S. Kishore
*Attorney, Agent, or Firm*—Rosanne Goodman

[57] ABSTRACT

This invention provides liposomes containing one or more N-acylated phosphatidylethanolamines, such liposomes being useful for localizing the delivery of bioactive agents to cells.

51 Claims, 9 Drawing Sheets

(3 of 9 Drawing Sheet(s) Filed in Color)

OTHER PUBLICATIONS

Fahey, "Surface Properties of 1,2–Dipalmitoyl–3–acyl–sn–glycerols," (1986) Biochemistry 25, 4468–4472.

Gruner, S. M. (1985) Proc. Natl. Acad. Sci. USA 82, 3665–3669.

Lafrance, et al., "Study of the Structure of N–Acyldipalmitoylphosphatidylethanolamines in Aqueous Dispersion by Infrared and Raman Spectroscopies," (1990) Biochemistry 29, 4592–4599.

Lee, et al., "Hydrophobic Alkyl Headgroups Strongly Promote Membrane Curvature and Violate the Headgroup Volume Correlation Due to "headgroup" Insertion", (1996) Biochemistry 35, 3677–3684.

Leventis, et al., "pH–Dependent Stability and Fusion of Liposomes Combining Protonatable Double–Chain Amphiphiles with Phosphatidylethanolamine," Biochem 1967, 26, 3267–3276.

Litzinger, et al., "Phosphatidylethanolamine liposomes: drug delivery, gene transfer and immunodiagnostic applications," (1992) Biochim. Biochem. Acta 1113, 201–227.

Mercadal, et al., "N–Palmitoylphospateidylethanolamine stabilizes liposomes in the presence of human serum: effect of lipidic composition and system characterization," (1995) Biochim. Biophys. Acta 1235, 281–288.

Newman, et al., "Phase Behavior of Synthetic N–Acylethanolamine Phospholipids," (1986) Chem. Phys. Lipids 42, 249–260.

Ortiz, et al., "Cation–induced aggregation and fusion of N–acyl–N–methyl–phosphatidylethanolamine vesicles," Chem Phys Lipids, 61(1992), 185–191.

Portis, et al., "Studies on the Mechanism of Membrane Fusion: Evidence for an Intramembrane $Ca^{2+}$–Phospholipid Complex, Synergism with $Mg^{2+}$, and Inhibition by Spectrin," (1979) Biochemistry 18, 780–790.

Verkleij, A. J. "Lipidic intramembranous particles," (1984) Biochim. Biophys. Acta 799, 43–63.

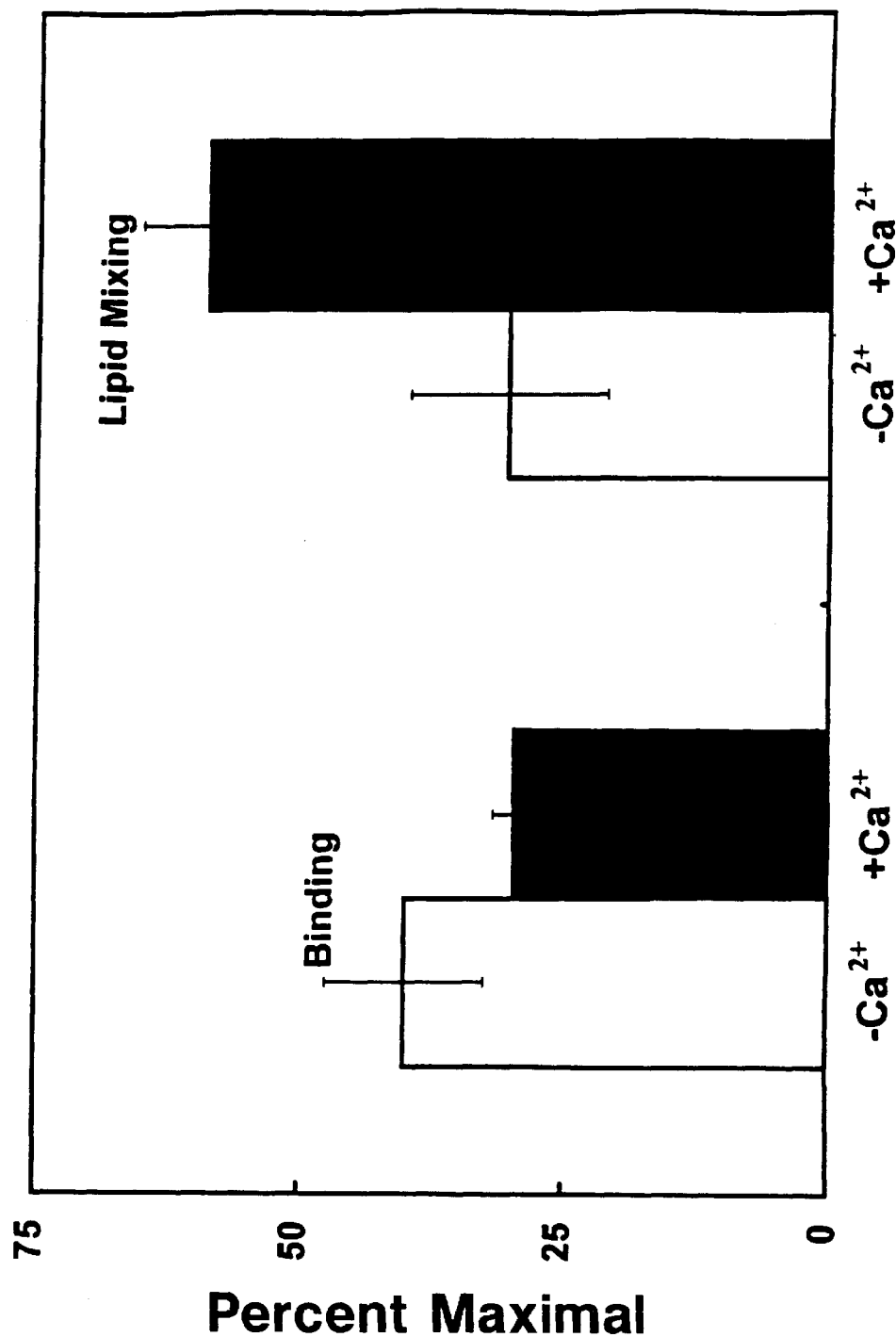

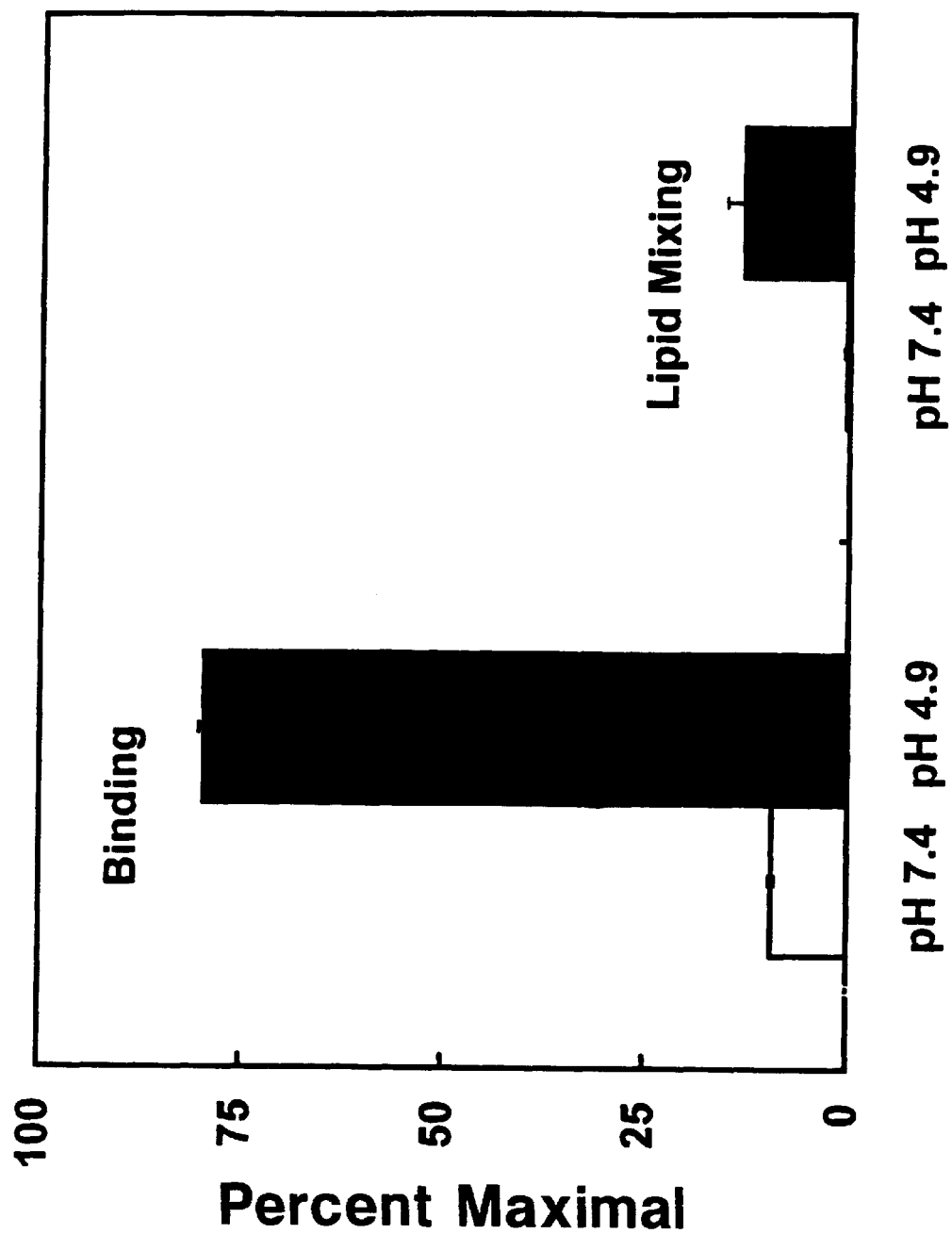

N-ACYL PHOSPHATIDYLETHANOLAMINE-MEDIATED LIPOSOMAL DRUG DELIVERY

This application is a continuation-in-part of provisional application U.S. Ser. No. 60/028,557 filed on Oct. 10, 1996.

FIELD OF THE INVENTION

This invention is directed to methods of delivering drugs to cells, by incorporating the drugs into, or associating the drugs with, liposomes containing an N-acyl phosphatidylethanolamine ("NAPE"), and then contacting the cells with the liposomes.

BACKGROUND OF THE INVENTION

Phosphatidylethanolamines ("PEs") are naturally occurring phospholipids typically having two acyl chains, as well as a phosphorylethanolamine group, attached to the lipid's glycerol backbone. N-acylated phosphorylethanolamines ("NAPEs") are PEs to which an additional, third acyl chain has been attached, by way of the amino moiety of the lipids' phosphorylethanolamine group. Some NAPEs are also found in biological membranes, in small amounts.

Most PEs ordinarily do not organize into bilayers at neutral pH, instead forming hexagonal ($H_{II}$)-phase structures in aqueous environments. Hexagonal-phase formation is a property that may be associated with enhanced liposome fusogenicity when these lipids are incorporated into liposomal bilayers under appropriate conditions (Verkleij, 1984; Cullis & de Kruijff, 1979; Ellens et al., 1989). NAPEs, by contrast, spontaneously form bilayers in aqueous dispersions, in the absence of added divalent cations (Newman et al., 1986; Akoka et al., 1988; Lafrance et al., 1990; Domingo et al., 1994).

None of the above documents describes a study of NAPEs with regard to their ability to be either fusogenic or bilayer-destabilizing at the desired delivery site, yet still be able to form liposomes that can stably encapsulate material. None of the previous studies describe the use to which NAPEs can be put to for the controlled delivery of liposomal drugs, and none describe tailoring NAPEs so as to optimize such delivery, especially in vivo. Moreover, none have either synthesized or studied the NAPE N-dodecanoyl dioleoyl phosphatidylethanolamine.

SUMMARY OF THE INVENTION

This invention provides liposomes containing a destabilization effective amount of an N-acyl phosphatidylethanolamine ("NAPE"), the liposomes being useful for fusion to cell membranes in the presence of suitable concentrations of cations and when placed adjacent to the cells. NAPEs are glycerol-based phospholipids having 14–24 carbon-long, saturated or unsaturated acyl chains attached at the first and second positions of the glycerol backbone. The third position is occupied by a phosphorylethanolamine, its amino group having a third acyl chain attached to it which is 4–24 carbon atoms long and saturated or unsaturated. Presently, the preferred NAPE is N-C12 DOPE (N-dodecanoyl dioleoyl phosphatidylethanolamine).

The destabilization effective amount of the NAPE contained in the liposome's lipid component is typically from about 10 mole % of the lipid component to about 90 mole %. The liposome into which the NAPE is incorporated can be a unilamellar, oligolamellar or multilamellar liposome, but is preferably unilamellar. The liposome's lipid component comprises, in addition to the NAPE, at least one other lipid. Such additional lipids include, without limitation, any of the types of lipids, e.g., phospholipids, glycolipids and sterols, which may be used in the preparation of liposomes.

Preferably, the additional lipid comprises one or more phospholipids. Most preferably, these include a phosphatidylcholine ("PC"), such as dioleoyl phosphatidylcholine ("DOPC") or a phosphatidylethanolamine ("PE"), e.g.: a PE selected from the group consisting of transesterified phosphatidylethanolamine, dipalmitoyl phosphatidylethanolamine, palmitoyl oleoyl phosphatidylethanolamine and dioleoyl phosphatidylethanolamine; or a PE conjugated to a moiety selected from the group consisting of dicarboxylic acids, polyethylene glycols, polyalkyl ethers and gangliosides.

The liposome can have a targeting moiety attached, and can contain, in either a bilayer or an aqueous compartment, one or more bioactive agents. Attachment of targeting moieties to the liposomes is preferred herein, so as to place the liposomes adjacent to the cells being targeted for delivery of the liposomes' contents, where the liposomes, in the presence of suitable concentrations of cations, can become locally destabilized or fuse to the cells.

This invention's liposomes can thus be used to deliver bioactive agents to cells, by contacting the cells with the liposomes under conditions in which the NAPE destabilizes the liposomes' bilayers, so as to induce local release of the liposomes' bioactive agent content and/or fusion of the liposome with the cells. Such delivery can be in vitro or in the body of a mammal, and can be used, e.g., for ex vivo stem cell transfection or in vivo delivery of anticancer therapeutic agents.

BRIEF DESCRIPTION OF THE DRAWINGS

The file of this patent contains at least one drawing/photograph executed in color. Copies of this patent with color drawing(s)/photograph(s) will be provided by the Patent and Trademark Office upon request and payment of the necessary fee.

FIG. 4. Comparison of DOPG/DOPC— (80:20), brain PS/DOPC— (80:20), and N-C12-DOPE/DOPC (80:20)- containing liposomes in terms of binding (A) and lipid mixing (B) with erythrocyte ghosts, measured by the NBD/Rh RET assay. The liposomes and ghosts were incubated at 37° C. for 1 hour in the presence of 3 mM Ca$^{2+}$. Y-axes: (A): % maximum binding; (B) % maximum mixing.

Figure 5A:
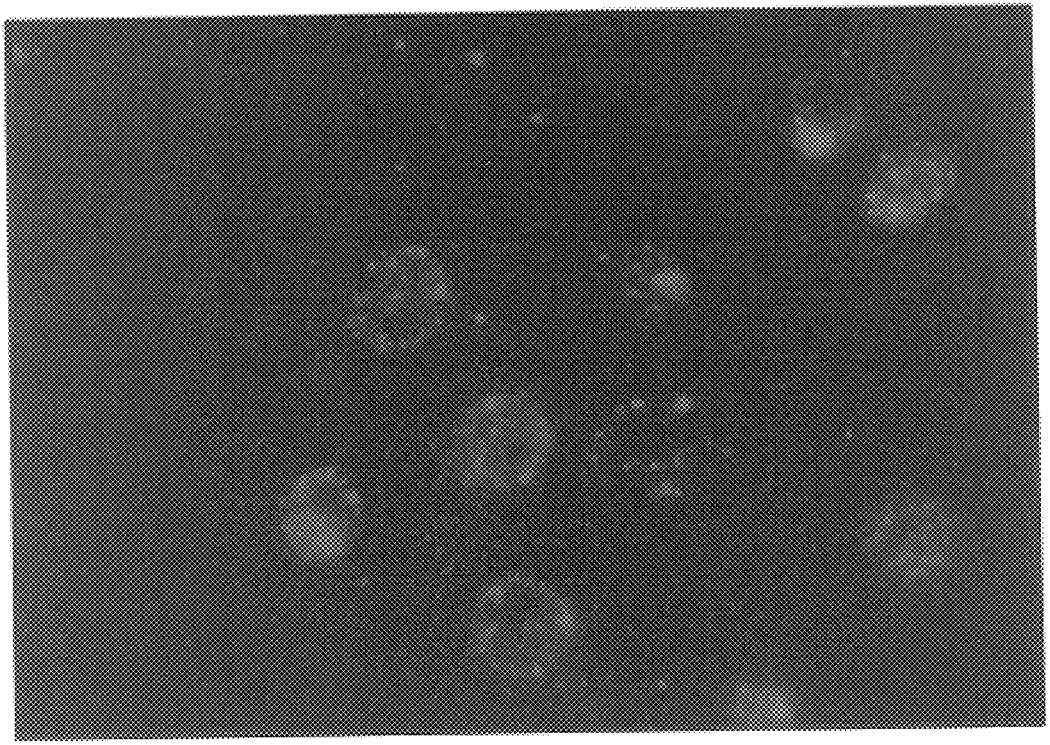
Figure 5B:
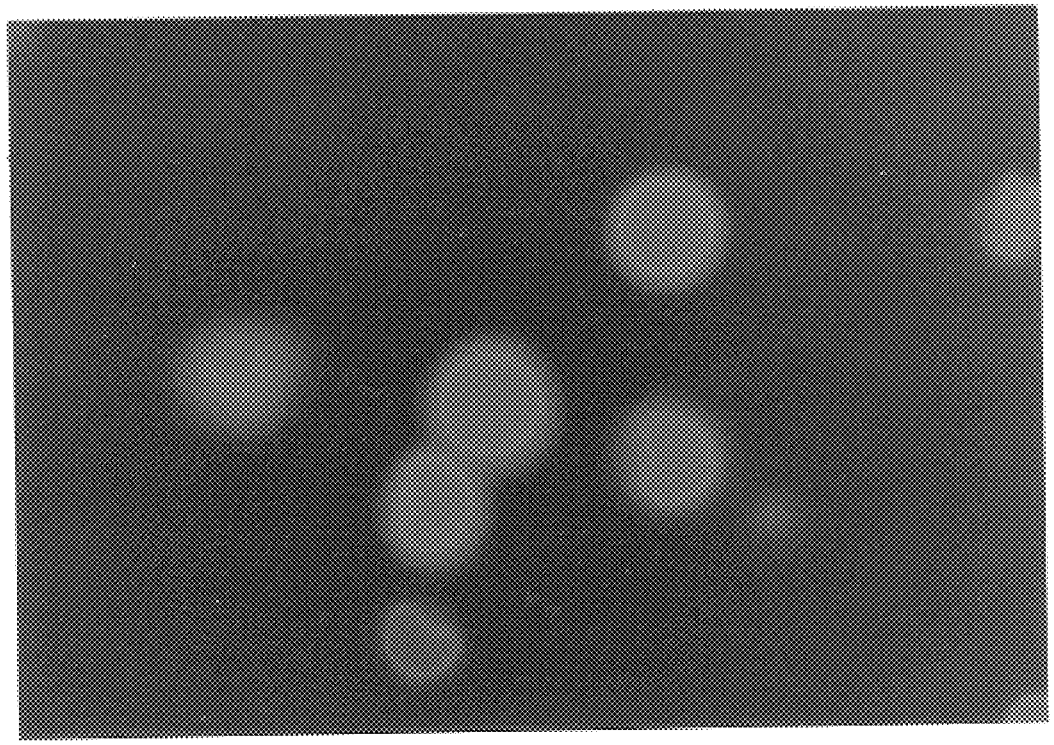
Figure 6A:
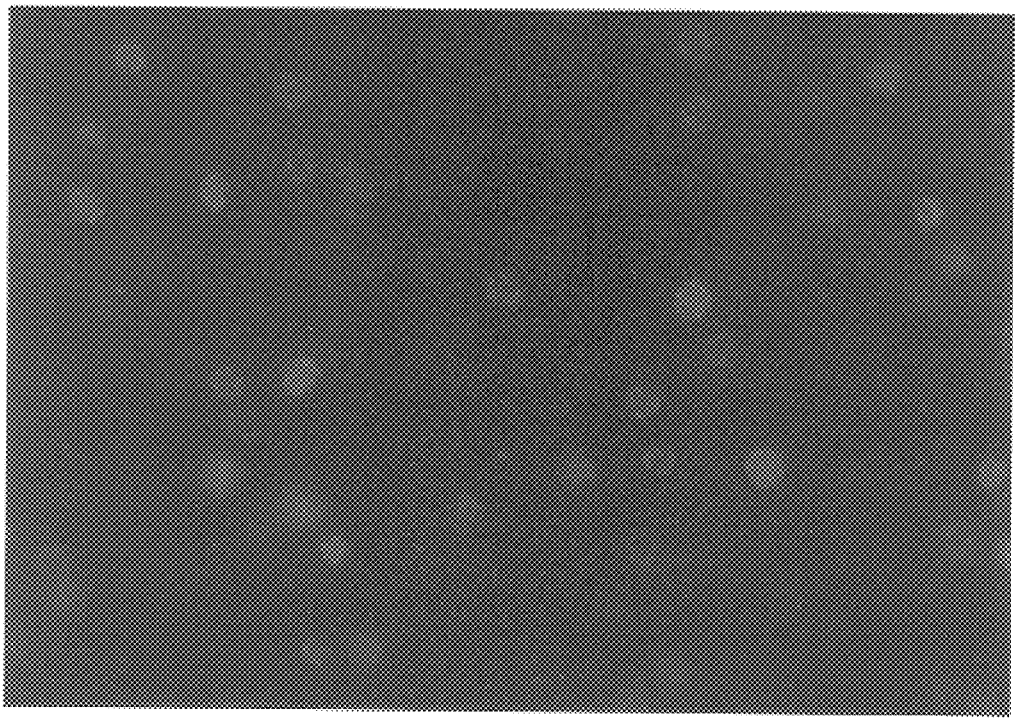
Figure 6B:
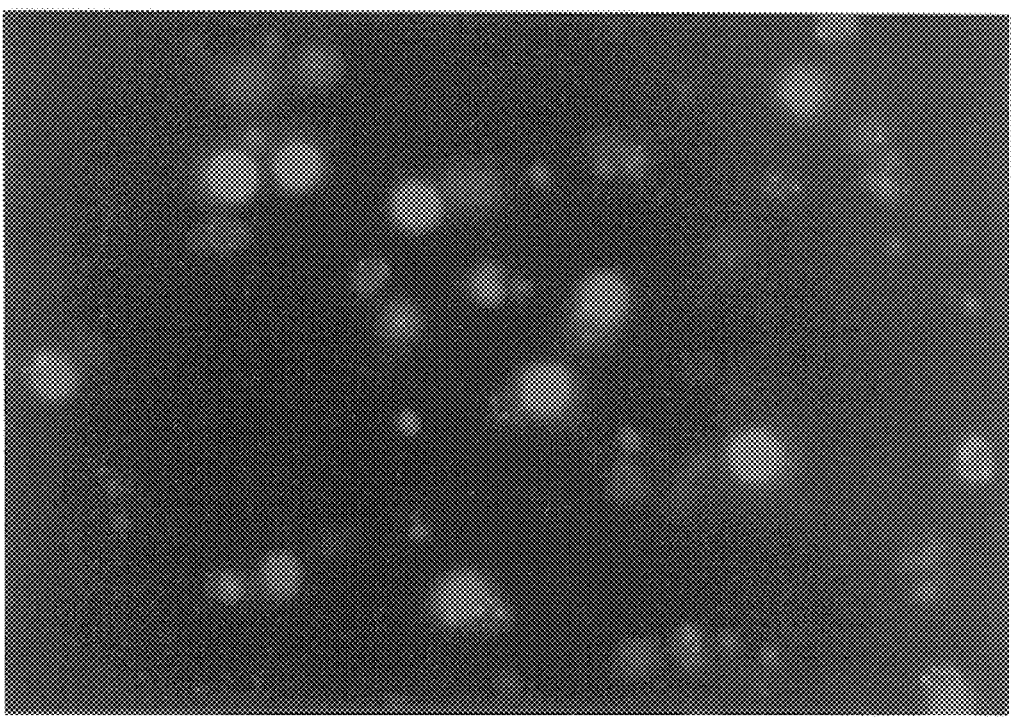
Figure 6C:
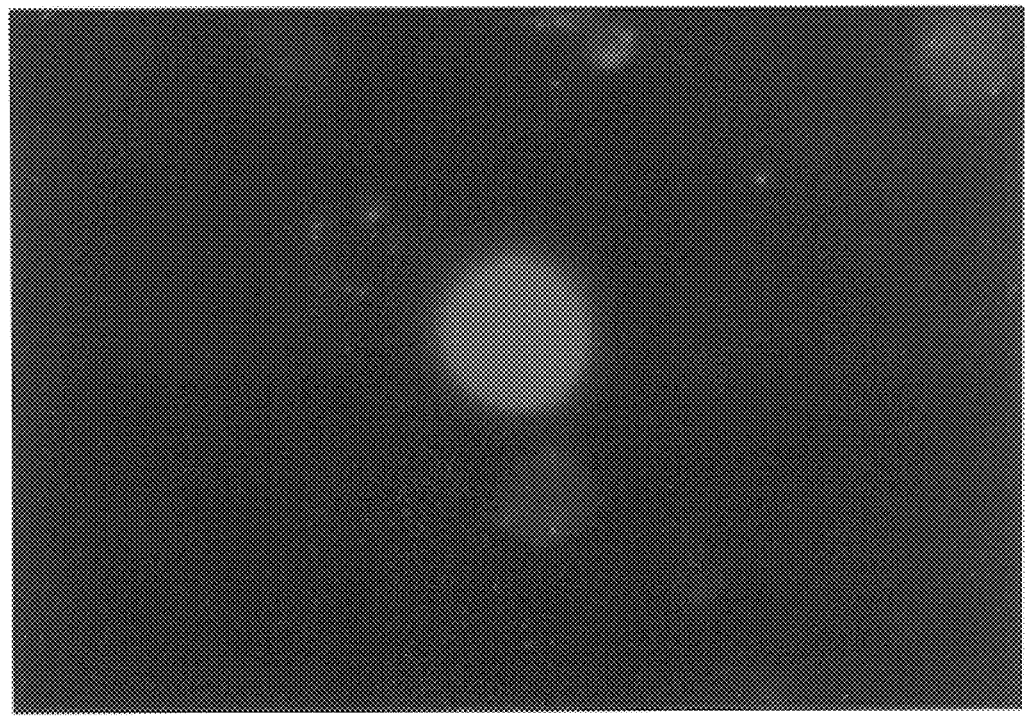
Figure 6D:

FIG. 5. Fluorescence micrographs of lipid mixing between N-C12-DOPE/DOPC (70:30) liposomes and erythrocyte ghosts. The NBD/Rh labeled liposomes were incubated with ghosts for 30 minutes without (A) or with (B) 1.25 mM Ca$^{2+}$/Mg$^{2+}$. After the incubation, the ghosts were washed to remove unbound liposomes. The total magnification is 1000× for each micrograph.

FIG. 6. Fluorescence micrographs of contents delivery from N-C12-DOPE/DOPC (70:30) liposomes into erythrocyte ghosts at 37° C. The TMR-70 kD dextran encapsulated liposomes were incubated with ghosts for 30 minutes without (A) or with (B & C) 1.25 mM Ca$^{2+}$/Mg$^{2+}$. In panel D, the ghosts were incubated for 30 minutes with free TMR-70 kD dextran in the presence of 1.25 mM Ca$^{2+}$/Mg$^{2+}$. After the incubation, the ghosts were washed to remove unbound liposomes. The total magnification is 400× for panels A, B, & D and 1000× for panel C.

FIG. 7. Binding and lipid mixing between N-C12-DOPE/DOPC (70:30) liposomes and U-937 cells, measured by the NBD/Rh RET assay. The liposomes and U-937 cells were incubated at 37° C. for 1 hour with or without 3 mM Ca$^{2+}$. Y-axis: % maximum binding (left-most columns) or mixing (right-most columns).

FIG. 8. pH-dependence of binding and lipid mixing between N-C12-DOPE/DOPC (70:30) liposomes and erythrocyte ghosts, measured by the NBD/RhRET assay. The liposomes and ghosts were incubated at the indicated pH for 1 hour, in the absence of divalent cations. Y-axes: (A): % maximum binding; (B) % maximum lipid mixing.

DETAILED DESCRIPTION OF THE INVENTION

Following are abbreviations to be found in this application, as well as the full names of the compounds designated by the abbreviations: PE, phosphatidylethanolamine; PC, phosphatidylcholine; PG, phosphatidylglycerol; PS, phosphatidylserine; DO—, dioleoyl—; NAPE, N-acyl phosphatidylethanolamine; NAE, N-acyl ethanolamine; N-C12-DOPE, N-dodecanoyl-dioleoyl phosphatidylethanolamine; NBD-PE, N-(7-nitro-2,1,3,-benzoxadiazol-4-yl) phosphatidylethanolamine (transesterified from egg phosphatidylcholine); Rh-PE, N-(lissamine rhodamine B sulfonyl)phosphatidylethanolamine (transesterified from egg phosphatidylcholine); TMR, tetramethylrhodamine; TMR-70 kD dextran, tetramethylrhodamine-conjugated 70 kD dextran; C$_{12}$E$_8$, octaethylene glycol monododecyl ether; RET, resonance energy transfer; LUV, large unilamellar liposome; TES, N-[tris(hydroxymethyl)methyl]-2-aminoethanesulfonic acid; $^1$H-NMR, proton nuclear magnetic resonance; H$_{II}$, hexagonal II; TLC, thin layer chromatography; and, BSA, bovine serum albumin.

This invention provides a liposome having a lipid component which comprises an N-acyl phosphatidylethanolamine ("NAPE"). NAPEs are phosphatidylethanolamines having three acyl chains, two attached directly to the glycerol backbone, and the third chain being attached by way of the headgroup's amine moiety. NAPEs thus have the following general structure

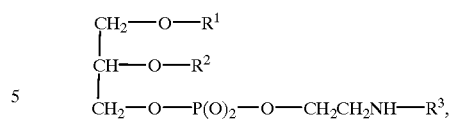

wherein each of R$^1$, R$^2$ and R$^3$ is an acyl chain having the structure: —C(O)(CH$_2$)$_{n1}$(CH═CH)$_{n2}$(CH$_2$)$_{n3}$(CH═CH)$_{n4}$ (CH$_2$)$_{n5}$(CH═CH)$_{n6}$(CH$_2$)$_{n7}$(CH═CH)$_{n8}$(CH$_2$)$_{n9}$CH$_3$. n1 is an integer equal to from 1 to 22; n3 is an integer equal to from 1 to 19; n5 is an integer equal to from 1 to 16; n7 is an integer equal to from 1 to 13; and, n9 is an integer equal to from 1 to 10. The acyl chains can be saturated, or unsaturated; that is, each of n2, n4, n6 and n8 is independently equal to 0 or 1.

The acyl chains attached directly to the NAPE's glycerol backbone, i.e., R$^1$ and R$^2$, are of a length suitable for stable bilayer formation. Accordingly, the sum of n1+2n2+n3+2n4+n5+2n6+n7+2n8+n9, designating the length of the acyl chain in numbers of carbon atoms is an integer equal to from 12 to 22 and each of R$^1$ and R$^2$ is, independently, from 14 to 24 carbon atoms in length. Preferably, each of R$^1$ and R$^2$ is 16–18 carbons in length. At least one of R$^1$ and R$^2$ is unsaturated, to aid in the transformation of the NAPE from a bilayer-preferring to bilayer-destabilizing phase, and at least one of n2, n4, n6 and n8 is therefore equal to 1. More preferably, both R$^1$ and R$^2$ are unsaturated, that is, for each of R$^1$ and R$^2$, at least one of n2, n4, n6 and n8 is equal to 1. Most preferably, R$^1$ and R$^2$ are each oleic acid, i.e., each is 18 carbons long, contains a single double bond, and has the structure —C(O)(CH$_2$)$_7$(CH═CH)(CH$_2$)$_7$CH$_3$.

The acyl chain attached to the amino group of the NAPE's phosphorylethanolamine can be 4 to 24 carbons long. That is, for R$^3$, the sum of n1+2n2+n3+2n4+n5+2n6+n7+2n8+n9 is equal to an integer of from 2 to 22; preferably, this sum is an integer equal to from 6 to 20. Preferably, the acyl chain is saturated. More preferably, R$^3$ is saturated and 12 carbons long.

Most preferably, the NAPE incorporated into liposomes comprises two oleic acid chains plus a 12-carbon chain attached to the amino group, and has the structure:

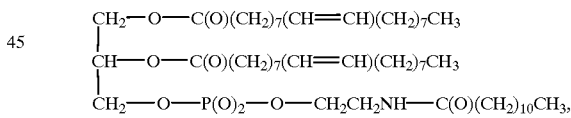

i.e., is N-dodecanoyl dioleoyl phosphatidylethanolamine ("N-C12 DOPE").

NAPEs are naturally occurring lipids, having been isolated from plants, microorganisms and animals (Bomstein, 1965; Clarke et al., 1976; Dawson et al., 1969; Ellingson 1980; Epps et al., 1979; Epps et al., 1980; Ganley et al., 1958; Gray & Yardly, 1975; Hargin & Morrison, 1980; Hazlewood & Dawson, 1975; Kuehl Jr. et al., 1957; MacMurray et al., 1970; Matsumoto & Miwa, 1973; Morrison et al., 1975; Natarajan et al., 1982; Natarajan et al., 1985; Reddy et al., 1984; Schmid et al., 1983; Schmid et al., 1990; Somerharju & Renkonen, 1979, the contents of which are incorporated herein by reference). NAPEs can also be produced synthetically, for example, as described in Example 1 hereinbelow. Briefly, such synthetic production involves dissolving a phosphatidylethanolamine ("PE"), e.g., DOPE, in an organic solvent, e.g., methylene chloride. The anhydride form of the fatty acid to be attached to the PE's amino group, e.g., lauric anhydride, is then added to the PE solution. Following chromatographic purification, the resulting compound is pooled and concentrated under vacuum; it can then be characterized by a variety of means, including proton nuclear magnetic resonance.

The liposome's lipid component contains a "destabilization-effective" amount of the NAPE, which is the amount of the NAPE that, when incorporated into a liposome's bilayer, is sufficient to destabilize that bilayer in the presence of suitable, e.g., physiological, concentrations of cations. "Bilayer destabilization" as used herein means disturbance or disruption of the lipid organization of a liposomal lipid bilayer so as to permit local release of the liposome's contents, and/or induce fusion of the liposome to other lipid layers, e.g., to cell membranes, when these are contacted by the liposome. A destabilization-effective amount of a NAPE is that amount of the NAPE which induces a greater degree of bilayer instability, under suitable conditions, than would be the case if the bilayer did not contain the NAPE. Destabilization effective amounts of NAPEs typically comprise at least about 10 mole % of the liposome's lipid component. Preferably, this amount is from about 10 mole % to about 90 mole % of the lipid component, more preferably, from about 20 mole % to about 80 mole % of the lipid component. Most preferably, presently, the NAPE comprises about 70 mole % of the lipid component.

In this regard, it is believed that the acylation of PEs so as to generate NAPEs produces charge on the PEs that eliminate the PEs' tendency to form nonbilayer phases; this charge effect thus is believed to allow the NAPEs to form stable bilayers. The presence of sufficient concentrations, e.g., at physiological levels, of various cations, e.g., $H^+$, $Ca^{2+}$ or $Mg^{2+}$, offsets this charge-counteracting effect of the third acyl chain, thus making the NAPEs themselves then unstable in bilayer conformation. Accordingly, the "suitable conditions" described herein for NAPE-containing bilayer destabilization include the presence of sufficient concentrations of one or more cations, as may be found in biological fluids or may be established in culture.

Delivery of liposome contents can readily be assessed by ordinarily skilled artisans given the teachings of this invention, using routine techniques. For example, the artisans can entrap a detectable marker in liposomes containing/not containing a NAPE, incubate those liposomes in suitable cell culture medium and then determine the percentage of detectable marker delivered into cells after the incubation. Following such experiments, the artisans would observe that cells incubated with NAPE-containing liposomes would contain a greater amount of detectable marker than would cells incubated with liposomes not containing a NAPE.

The liposome's lipid component contains, in addition to the NAPE, another lipid. Such additional lipids can be any of the various types of lipids, e.g., phospholipids, glycolipids, or sterols, commonly used in liposomes. Preferably, the additional lipid comprises one or more phospholipids, e.g., a phosphatidylcholine ("PC") such as dioleoyl phosphatidylcholine ("DOPC"). For example, in certain preferred embodiments of this invention, the additional lipid is DOPC, the liposome's lipid component comprises about 30 mole % DOPC and about 70 mole % of the NAPE N-dodecanoyl dioleoyl phosphatidylethanolamine.

The additional lipid can also be a phosphatidylethanolamine ("PE"), such as transesterified PE ("tPE"), dipalmitoyl PE ("DPPE"), palmitoyloleoyl PE ("POPE"), dioleoyl PE ("DOPE"), or a PE the headgroup of which is derivatized with a moiety selected from the group consisting of dicarboxylic acids, polyethylene glycols, polyalkyl ethers and gangliosides. Such moieties are capable of inhibiting the binding of serum proteins to liposomes into which the lipids have been incorporated. Accordingly, PEs containing such headgroup modifications, "headgroup-modified lipids," alter the pharmacokinetic behavior of the liposomes, prolonging their circulatory half-lives and increasing the proportion of the parent liposomes which reach intended sites of therapeutic or diagnostic action (see, e.g., Blume et al., Biochim. Biophys. Acta. 1149:180 (1993); Gabizon et al., Pharm. Res. 10(5):703 (1993); Park et al. Biochim. Biophys. Acta. 1108:257 (1992); Woodle et al., U.S. Pat. No. 5,013,556; and Allen et al., U.S. Pat. Nos. 4,837,028 and 4,920,016, the contents of which are incorporated herein by reference).

Preferred headgroup-modified lipids comprise phosphatidylethanolamines-dicarboxylic acid ("PE-DCAs") or polyethylene glycol conjugates. Presently, the most preferred headgroup-modified lipid is dioleoyl phosphatidylethanolamine ("DOPE-GA"). The amount of a headgroup-modified lipid incorporated into a liposome depends upon a number of factors well known to the ordinarily skilled artisan, or within his purview to determine without undue experimentation. These include, but are not limited to: the type of headgroup modification; the type and size of the liposome; and the intended therapeutic use of the formulation. Preferably, headgroup-modified lipids are incorporated into liposomes at a concentration of at least about 5 mole % of the liposome's lipid component, more preferably about 10 mole % of the lipid component.

"Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium, while the acyl chains reorient towards the interior of the bilayer. A stable structure is thus formed in which the acyl chains are effectively shielded from contact with the surrounding aqueous medium.

Unilamellar liposomes are liposome having a single lipid bilayer, and can be either small unilamellar liposomes ("SUVs"), having an average diameter of 25–50 nm, or large unilamellar liposomes ("LUVs"), having an average diameter of greater than 50 nm. Oligolamellar liposomes have from 1 to several lipid bilayers, and multilamellar liposomes ("MLVs") have multiple bilayers. The liposome of this invention can be unilamellar, oligolamellar or multilamellar, but is preferably unilamellar, and more preferably, a large unilamellar liposome.

Liposomes can be made by a variety of methods (for a review, see, e.g., Deamer and Uster (1983)). Multilamellar liposomes can be made, for example, by the method of Bangham et al. (1965), and by the methods of Lenk, Fountain or Cullis for making MLVs with substantially equal interlamellar solute distribution (i.e., "SPLVs"; see, U.S. Pat. Nos. 4,522,803, 4,588,578, 5,030,453, 5,169,637 and 4,975,282). Oligolamellar liposomes can be made, for example, by Boni's method of making interdigitation-fusion ("IF") liposomes (see, EP Patent No. 510,086), or by Papahadjopoulos' reverse-phase evaporation technique (U.S. Pat. No. 4,235,871). Unilamellar liposomes can be made by methods such as ethanol injection (see, e.g., Batzri and Kron, 1973), or from MLVs using such techniques as sonication (Papahadjopoulos et al. (1968)) or extrusion (U.S. Pat. Nos. 5,008,050 and 5,059,421). The liposome of this invention can be produced by any method generally accepted in the art for making liposomes, including, without limitation, the methods of the above-cited documents (the contents of which are incorporated herein by reference).

Liposomes of this invention can be dehydrated, stored and then reconstituted such that a substantial portion of the liposomes' contents are retained through the dehydration/rehydration process. Liposomal dehydration generally requires use of a hydrophilic drying protectant at both the inside and outside surfaces of the liposomal bilayers (see U.S. Pat. No. 4,880,635, the contents of which are incorporated herein by reference). This hydrophilic compound is generally believed to prevent the rearrangement of the lipids in the liposome, so that the size and contents are maintained during the drying procedure, and through subsequent rehydration. Most preferably, the drying protectant is a disaccharide sugar, e.g., lactose, maltose, trehalose or sucrose.

The liposome of this invention can comprise a "targeting moiety," i.e., a moiety that can be attached to a liposome and which can then direct the liposome to a specific site within the body of a mammal. Such directed delivery is generally believed to occur as a result of the recognition by the targeting moiety of a compound on the surface of the cells being targeted. Typical targeting moieties include, without limitation, antibodies, cell receptor ligands, lectins and the like. Targeting moieties can be attached to liposomes by any of the means generally accepted in the art for the covalent or noncovalent attachment of such moieties to liposomes. Such means include, for example and without limitation, those described in the following documents, the contents of which are incorporated herein by reference: U.S. Pat. No. 5,399,331 describes the coupling of proteins to liposomes through use of a crosslinking agent having at least one maleimido group and an amine reactive function; U.S. Pat. Nos. 4,885,172, 5,059,421 and 5,171,578 link proteins to liposomes through use of the glycoprotein streptavidin; Sato and Sunamoto describe the coating of targeted liposomes with polysaccharides.

Also provided herein are compositions containing the liposomes of this invention. Included in such compositions are pharmaceutical compositions that also comprise a "pharmaceutically acceptable carrier," which is a medium generally acceptable for use in connection with the administration of liposomes to animals, including humans. Pharmaceutically acceptable carriers are formulated according to a number of factors well within the purview of the ordinarily skilled artisan to determine and account for, including without limitation: the particular bioactive agent used, its concentration, stability and intended bioavailability; the disease, disorder or condition being treated with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985), the contents of which are incorporated herein by reference). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, such as those which enhance the stability of the liposomes.

Further provided herein is a method of delivering a bioactive agent to a cell. "Bioactive agents" which may be delivered by the liposomes into cells are any compound or composition of matter that can be formulated in liposomes and administered to animals, preferably humans. Liposomes can be loaded with bioactive agents by solubilizing the agent in the lipid or aqueous phase used to prepare the vesicles. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056, the contents of which are incorporated herein by reference).

Bioactive agents can have therapeutic activity in animals, and can also be administered for diagnostic purposes. Bioactive agents which may be associated with this invention's liposome include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; nucleic acid sequences such as messenger RNA, cDNA, genomic DNA and plasmids; bioactive lipids such as ether lipids and ceramides; and the like.

The method of bioactive agent delivery of this invention comprises contacting the cell with a composition containing the liposome of this invention. Such contacting is preferably done in the presence of a suitable concentration, for example but not limited to, 1–3 mM of a cation, e.g., $Ca^{2+}$, $Mg^{2+}$ or a $Ca^{2+}/Mg^{2+}$ combination; the contacting can also be done at an acidic pH in the absence of additional cations.

Delivery can occur in vitro, such as for diagnostic purposes or for ex vivo delivery of a therapeutic agent or nucleic acid to bone marrow cells, in which case the liposome-containing composition also contains the divalent cation. Alternatively, the contacting can be in vivo, in which case the cells are preferably mammalian, a pharmaceutically acceptable carrier is used and the liposomes preferably comprise a targeting moiety. In vivo liposomal bioactive agent delivery according to the practice of this invention can deliver therapeutically or diagnostically effective amounts of therapeutic or diagnostic agents into the cells of a mammal afflicted with a disease, disorder or condition amenable to diagnosis or treatment with the agent. Hence, such delivery fusion can be used to diagnose or treat the mammal for the disease, disorder or condition. For example, the mammal can be afflicted with an infectious microbial disease, e.g., a viral or bacterial infection, cancer, e.g., a brain, breast, colon, lung, ovarian, prostate or stomach cancer, or inflammatory condition, e.g., an arthritic condition or autoimmune disorder such as rheumatoid arthritis or juvenile diabetes, and a therapeutically effective amount of an antimicrobial, anticancer or anti-inflammatory agent can be delivered to the mammal's cells.

The delivery of liposomal contents to cells is facilitated by the incorporation of NAPEs into liposomes, as the NAPEs can destabilize the liposomes' bilayers in the presence of suitable concentrations, e.g., physiological, of cations, or at an acidic pH in the absence of additional contents. NAPE-mediated destabilization can even lead to fusion of the liposomes to cell membranes, and hence for direct delivery of the liposomes' contents to the cells.

Fusion involves both liposome-cell binding and mixing of liposomal and cell membrane lipids, which can be assessed by a number of means well within the purview of ordinarily skilled artisans given the teachings of this invention to conduct. These means include, for example and without limitation, the fluorescence-based assays described more fully in Example 4 hereinbelow. Briefly, liposomes can be labeled with fluorescent markers, such as N-(7-nitro-2,1,3-benzoxadiazol-4-yl)phosphatidylethanolamine ("NBD-PE") and N-(lissamine rhodamine B sulfonyl) phosphatidylethanolamine ("Rh-PE"), and then combined with erythrocyte ghosts, i.e., red blood cells deprived of their hemoglobin content; erythrocyte ghosts are particularly suited for use in the assessment of liposome-cell fusion, as these cells are incapable of endocytosing the liposomes, and hence, of incorporating liposomal lipids into their cell membranes by means other than fusion. Erythrocyte ghosts can be prepared as previously described (see Williamson et al., 1985, and Clague et al., 1990, the contents of which are incorporated herein by reference), for example, by swelling erythrocytes in hypotonic solution so as to burst them and thereby release their hemoglobin, and then resealing the burst erythrocytes by incubation in a suitable buffer.

Labeled liposomes are incubated with erythrocyte ghosts in the presence of divalent cations, e.g., $Ca^{2+}$, $Mg^{2+}$, or $Ca^{2+}/Mg^{2+}$, at various concentrations, e.g., 1–3 mM. After removing unbound liposomes, the degree of liposome-ghost binding is assessed by measuring the amount of ghost-associated fluorescence. Lipid mixing is assessed by a number of means well known to ordinarily skilled artisans, including, for example, the resonance energy transfer ("RET") assay set forth in Example 4 hereinbelow (and described more fully in Struck et al., 1981, the contents of which are incorporated herein by reference).

Figure 1:
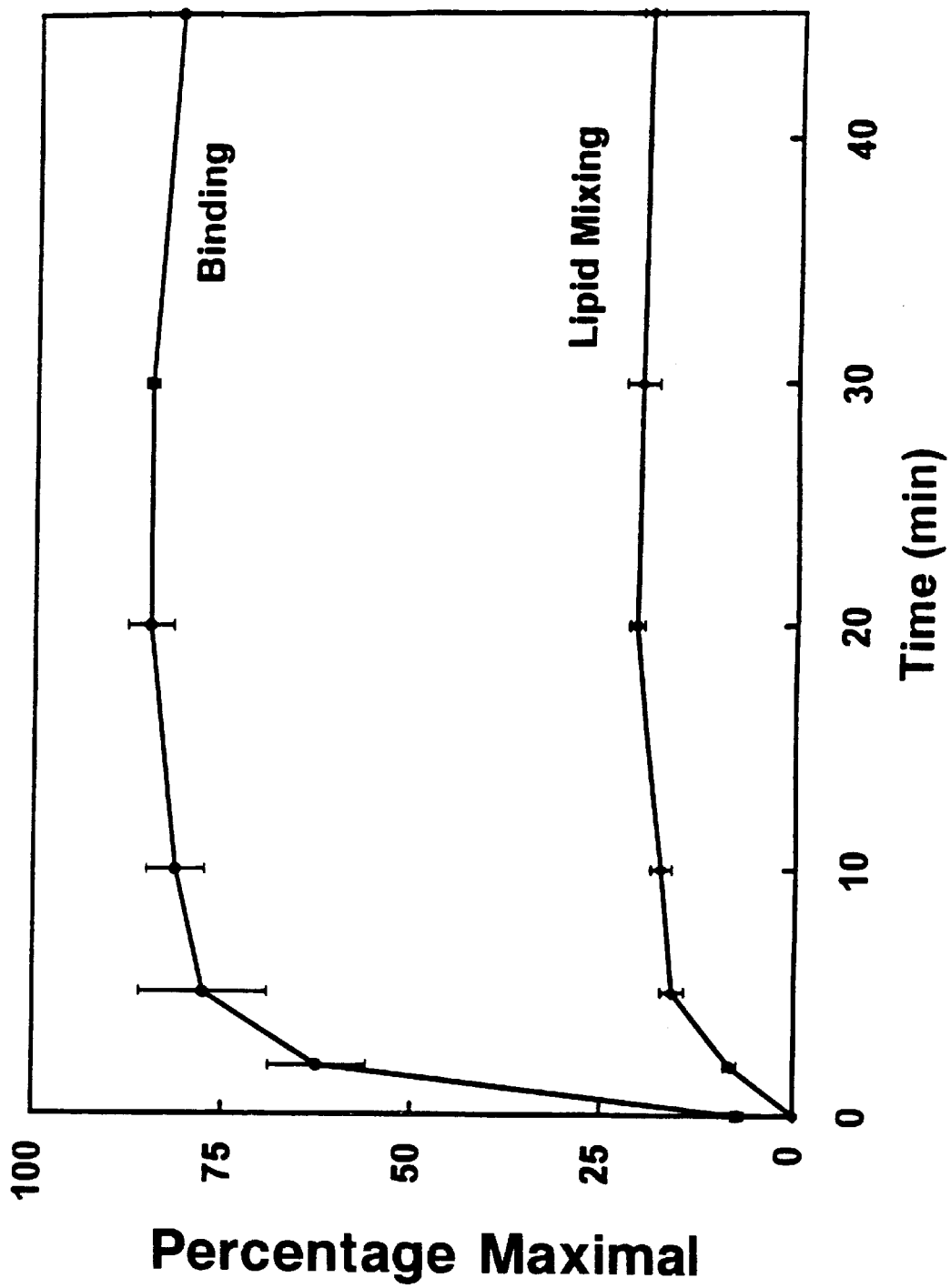
FIG. 1. Kinetics of binding and lipid mixing between N-C12-DOPE/DOPC (70:30) liposomes and erythrocyte ghosts at 37° C., measured by the NBD/Rh RET assay. The liposomes and ghosts were incubated at 37° C. for the indicated time periods in the presence of 3 mM $Ca^{2+}$; the NBD and Rh fluorescence were measured after the unbound liposomes were removed by centrifugation. Lipid mixing and binding are expressed as percentages of detergent values as described hereinbelow. Top curve: liposome binding; bottom curve: lipid mixing. X-axis: Time (min); y-axis % maximum liposome binding and lipid mixing.
Figure 2A:
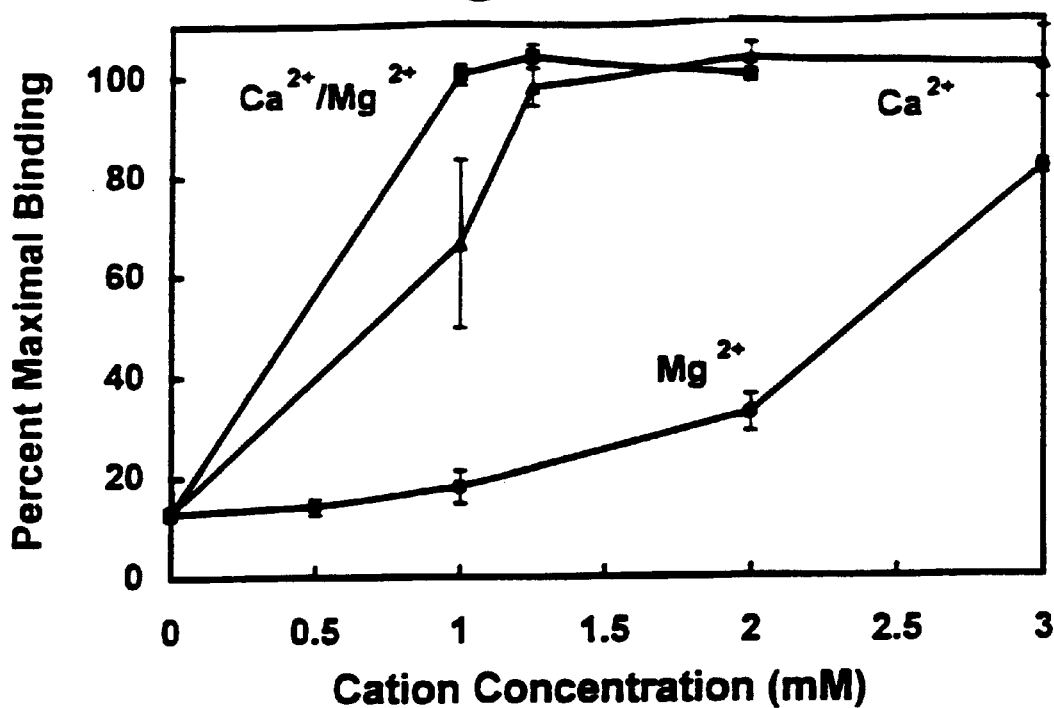
FIG. 2. Divalent cation-dependence of binding (A) and lipid mixing (B) between N-C12-DOPE/DOPC (70:30) liposomes and erythrocyte ghosts, measured by the NBD/Rh RET assay. The NBD/Rh-labeled liposomes and unlabeled ghosts were incubated at 37° C. for 1 hour in the presence of the indicated concentrations of cation(s). (A) and (B): filled squares: $Ca^{2+}/Mg^{2+}$; filled triangles: $Ca^{2+}$; filled circles: $Mg^{2+}$. X-axis: Cation concentration (mM); y-axes: (A): % maximum binding; (B) % maximum mixing.
Figure 2B:
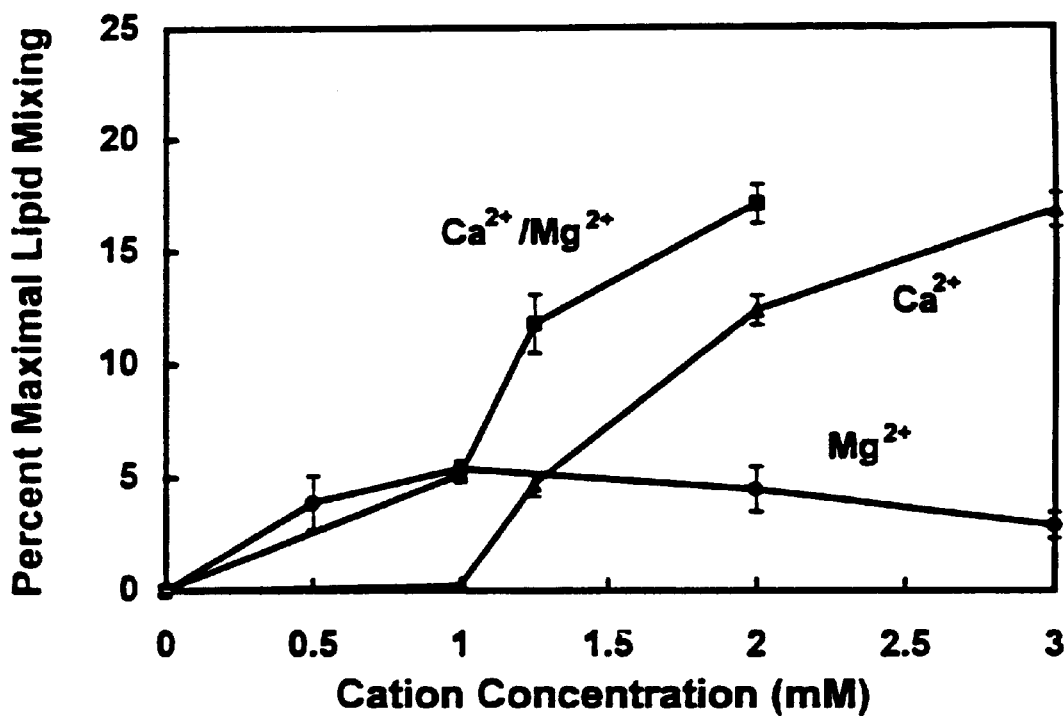
Figure 3A:
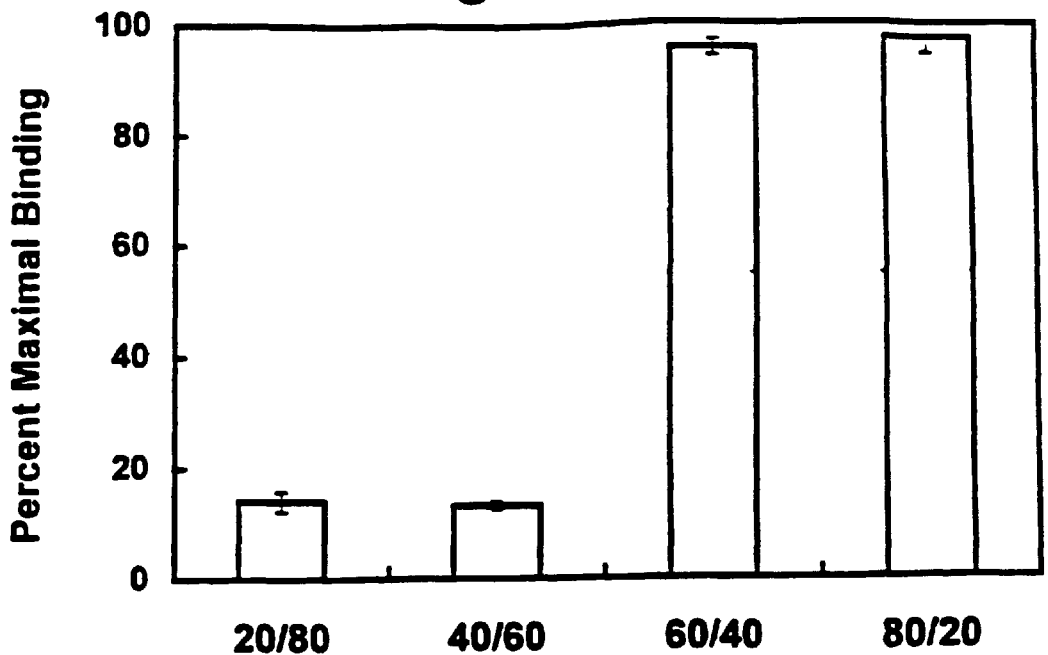
FIG. 3. N-C12-DOPE-dependence of binding (A) and lipid mixing (B), measured by the NBD/Rh assay. Labeled liposomes and unlabeled ghosts were incubated at 37° C. for 1 hour in the presence of 3 mM $Ca^{2+}$. X-axes: molar ratio of N-C12-DOPE: DOPC; y-axes: (A): % maximum binding; (B) % maximum mixing.
Figure 3B:
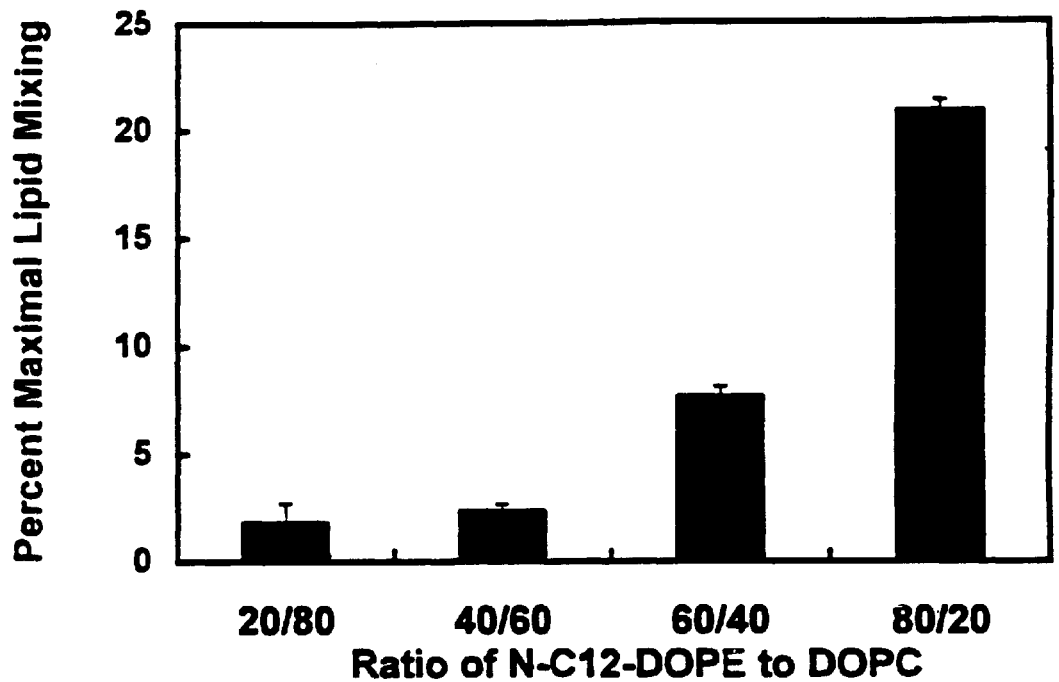
Figure 4A:
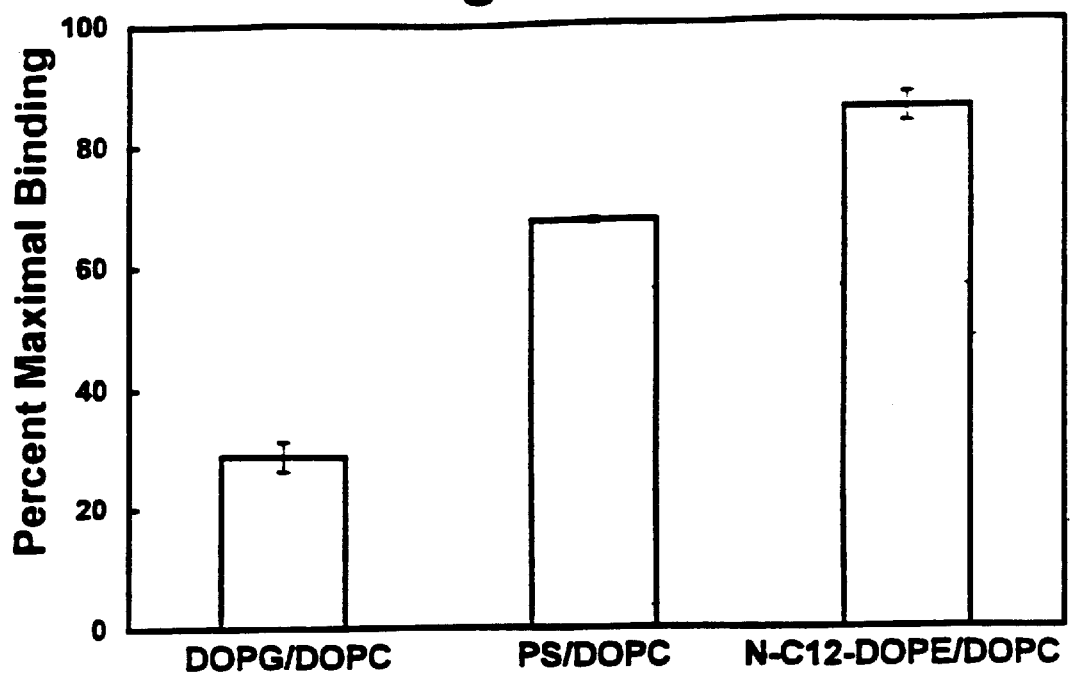
Figure 4B:
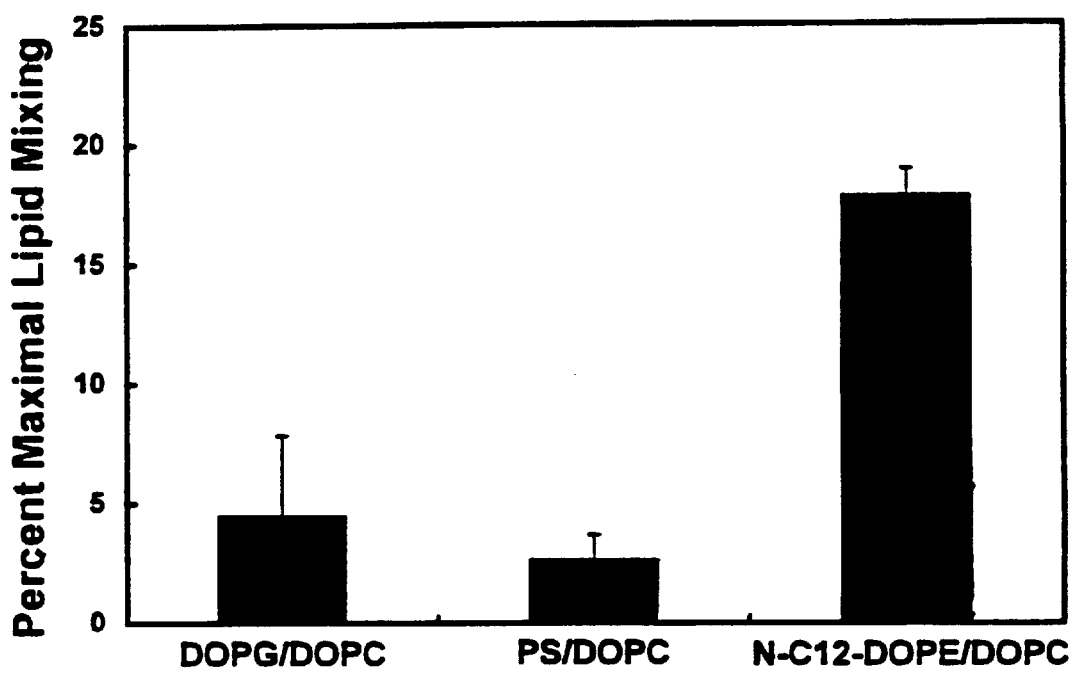

As shown in FIG. 2 herein, incubation of N-C12-DOPE/ DOPC liposomes (70 mole %/30 mole %) with erythrocyte ghosts, in the presence of 3 mM $Ca^{2+}$, resulted in liposome-erythrocyte binding as well as lipid mixing. Moreover, results depicted in FIGS. 4 and 5 herein clearly show that a NAPE, e.g., N-C12-DOPE, was required to be present in liposomes in order for the liposomes to fuse with cells. Furthermore, results (see FIG. 8) also show that binding and mixing, and hence, liposome-cell fusion, can occur in the absence of divalent cations, but at an acidic pH.

This invention will be better understood from the following Examples. However, those of ordinary skill in the art will readily understand these examples are merely illustrative of the invention, as defined in the claims which follow thereafter.

EXAMPLES

Materials: DOPC, brain PS, dioleoyl phosphatidylethanolamine (DOPE), dioleoyl phosphatidylglycerol (DOPG) were purchased from Avanti Polar Lipids (Alabaster, Ala.). N-(7-nitro-2,1,3,-benzoxadiazol-4-yl) phosphatidylethanolamine (egg) (NBD-PE), N-(lissamine rhodamine B sulfonyl)phosphatidylethanolamine (egg) (Rh-PE), tetramethylrhodamine B conjugated 70 kD dextran (TMR-70D) were purchased from Molecular Probes (Eugene, Oreg.). Octaethylene glycol monododecyl ether ($C_{12}E_8$) and triethylamine were purchased from Fluka (Ronkonkoma, N.Y.). N-[tris(hydroxymethyl)methyl]-2-aminoethanesulfonic acid (TES) was purchased from Calbiochem (La Jolla, Calif.). Lauric anhydride was purchased from Aldrich (Milwaukee, Wis.). Human prothrombin, factor V/VA, and factor Xa were purchased from Enzyme Research Laboratories, Inc. (South Bend, Ind.). Sarcosine-Pro-Arg-p-nitroanilide was purchased from Sigma (St. Louis, Mo.). U-937 cells were purchased from American Type Culture Collection (Rockville, Md.).

Example 1

NAPE Synthesis and Characterization

DOPE dissolved in $CHCl_3$ (500 mg, 0.67 mmol) was stirred for 24 hr at room temperature with lauric anhydride (513 mg, 1.34 mmol) and triethylamine (726 mg, 7.2 mmol). Thin layer chromatograph (TLC) analysis showed the disappearance of all starting materials. The solvent was evaporated and the residue was purified by flash column chromatography on a silica gel (230–400 mesh, Aldrich, Milwaukee, Wis.) using the solvent gradients of $CHCl_3$/ MeOH, 100:0, 98:2, 95:5, 90:10, and 80:20. The desired compound was pooled and concentrated under vacuum. The obtained product was dissolved in a minimum amount of $CHCl_3$ and the solution was passed through an Acrodisco® CR syringe filter (0.2 micron, Fisher Scientific, Malvern, Pa.) to remove the silica gel. After removal of chloroform, the product was lyophilized from cyclohexane and characterized by proton nuclear magnetic resonance ($^1H$ NMR, Bruker Instrument, Inc., Manning, Mass., 300 MHz, $CDCl_3$) and TLC. Larger quantities of N-C12-DOPE were purchased from Avanti Polar Lipids.

Example 2

Liposome Preparation

NBD/Rh labeled large unilamellar vesicles (LUVs) were prepared as described before (Mayer et al., 1986, the contents of which are incorporated herein by reference). Briefly, a mixture of 70 mole % N-dodecanoyl dioleoyl phosphatidylethanolamine and 30 mole % dioleoyl phosphatidylcholine, in chloroform, was dried under a nitrogen stream to a thin film, which was then left under vacuum overnight to remove residual solvent. The lipid film was then hydrated with TES buffered saline (10 mM TES, 0.1 mM EDTA, 154 mM NaCl, pH 7.4); brief vortexing was applied to ensure complete hydration. After ten cycles of freeze/thaw in a liquid nitrogen/room temperature water bath, the sample was extruded ten times through a 0.1-$\mu$m polycarbonate membrane filter (Poretics Corp., Livermore, Calif.). The resulting liposomes were stored at 4° C.

For dextran-encapsulated LUVs, no fluorescent lipid label was used. The dry lipid film was hydrated with 50 mg/ml TMR-70D in 10 mM TES buffered saline. After freeze/thaw and extrusion, the LUVs were separated from unencapsulated dextran by passing through a 45×1.3 cm Biogel-A50 gel filtration column (Bio-Rad Laboratories, Richmond, Calif.). LUVs eluted at the void volume. The liposomes were stored at 4° C. and used within one week after preparation. The phospholipid concentration of each liposome preparation was determined by phosphate assay (Bartlett, 1959). The approximately 0.1 $\mu$m size of the liposomes was confirmed on a Nicomp submicron particle sizer (Nicomp Instruments, Inc., Goleta, Calif.) using quasi-electric light scattering.

Example 3

Preparation of Resealed and Unsealed Human Erythrocyte Ghosts

Resealed ghosts are referred to as erythrocyte ghosts unless otherwise specified, and were prepared as previously described (Williamson et al, 1985 and Clague et al., 1990). Briefly, fresh human blood was washed several times with cold 10 mM TES buffered saline to remove plasma and white cells. Then 2 ml of washed erythrocytes (50% hematocrit) were preswelled in cold hypotonic solution containing 8 ml $H_2O$ and 9.6 ml 10 mM TES buffered saline. Preswelled erythrocytes were pelleted at 850×g for 5 minutes. The pellet was resuspended in 40 ml cold lysis buffer (10 mM Tris, 0.1% BSA, 2 mM $MgCl_2$, and 0.1 mM EGTA) and incubated on ice for at least 2 minutes. After addition of 4.5 ml 10x resealing buffer (1.22 M NaCl, 30 mM KCl, 0.15 M $Na_2HPO_4$, 50 mM $KH_2PO_4$, and 2 mM $MgCl_2$), the sample was incubated at 37° C. for 40 minutes. The resealed ghosts were pelleted at 1750xg for 10 minutes, and washed several times until no hemoglobin was observed in the supernatant. The resealed ghosts were stored at 4° C. and used within one week.

Unsealed erythrocyte ghosts were prepared as described before (Steck & Kant, 1974, the contents of which are incorporated herein by reference). Briefly, erythrocytes were washed several times with 10 mM TES buffered saline to remove plasma and white cells. The pellet was resuspended in cold 5 mM $Na_2HPO_4$, and spun at 14000xg for 15 minutes. The resulting pellet was washed with the same buffer until the supernatant was clear. The unsealed ghosts were stored in the same buffer at 4° C., and used within one week.

Example 4

Fluorescent Binding and Lipid Mixing Assays

For each assay, either 100 nmole of liposomes and $5 \times 10^8$ erythrocyte ghosts or 10 nmole of liposomes and $1 \times 10^7$ U-937 cells were mixed. The total volume was brought to 100 μl with 10 mM TES buffered saline. For assays at low pH, an equal volume of 50 mM citrate buffered saline (50 mM citrate, 90 mM NaCl, 0.1 mM EDTA, pH 4.7) and liposome-ghost mixture were mixed to yield a final pH of 4.9, and a final volume of 106 μl. The mixture was incubated at 37° C. for indicated periods of time with, or without, divalent cations. The mixture was then centrifuged for 5 minutes at 3500xg to pellet ghosts, or 300xg to pellet U-937 cells. The unbound liposomes were removed with the supernatant, and the pellet was resuspended in 100 μl of TES buffered saline, following which it was transferred to a cuvette containing the same buffer, at room temperature. The total volume in the cuvette was 2 ml. All the data are averages of three identical experiments unless otherwise specified.

Lipid mixing between NBD/Rh labeled liposomes and unlabeled ghosts or U-937 cells was measured in 10 mM TES buffered saline by the NBD/Rh resonance energy transfer (RET) assay (Struck et al., 1981). The NBD fluorescence was recorded at room temperature on a PTI Alphascan™ fluorometer (South Brunswick, N.J.) in a cuvette with continuous stirring. The excitation wavelength was 450 nm, with a 450±20 nm bandpass filter (Melles Griot, Irvine, Calif.) to further refine the light beam. The emission wavelength was 530 nm, with a >500 nm highpass filter (Schoft Glass Technologies, Duryea, Pa.). The NBD fluorescence of a freshly prepared liposome-cell mixture, i.e. without incubation and spin, was also measured with, and without, 0.2% $C_{12}E_8$ to give the 0% and 100% lipid mixing, respectively. The fluorescence of Rh in the presence of 0.2% $C_{12}E_8$ was used to measure liposome binding. The excitation wavelength was 560 nm with a 550±20 nm bandpass filter (Melles Griot, Irvine, Calif.) to further refine the light beam. The emission wavelength was 600 nm with a >570 highpass filter (Schoft Glass Technologies, Duryea, Pa.). The fluorescence level of cells alone in the presence of 0.2% $C_{12}E_8$ was taken as 0% binding. The Rh fluorescence of a freshly prepared liposome-cell mixture was also measured in the presence of 0.2% $C_{12}E_8$ to yield 100% binding. The extents of lipid mixing and binding were calculated as set forth hereinbelow.

$$\% \text{ lipid mixing} = 100 \times \frac{[(N_S - N_C) \times R_{OD} / R_{SD}] + N_C - N_0}{[(N_S - N_{CD}) \times R_{OD} / R_{SD}] + N_{CD} - N_0}; \text{ and,}$$

$$\% \text{ binding} = 100 \times \frac{R_{SD} - R_{CD}}{R_{OD} - R_{CD}},$$

wherein: $N_S$: NBD fluorescence of sample; $N_C$: NBD fluorescence of cells alone; $N_0$: NBD fluorescence of freshly prepared liposome-cell mixture; $N_{SD}$: NBD fluorescence of sample in the presence of detergent; $N_{CD}$: NBD fluorescence of cells alone in the presence of detergent; $R_{OD}$: Rh fluorescence of freshly prepared liposome-cell mixture in the presence of detergent; $R_{SD}$: Rh fluorescence of sample in the presence of detergent; and, $R_{CD}$: Rh fluorescence of cells alone in the presence of detergent.

Binding percentages for ghosts were corrected for the residual unbound fluorescence by essentially assuming 10% of the supernatant remained in each pellet. Therefore:

$$\% \text{ binding(corr.)} = 1.11(\% \text{ measured}) - 11.1$$

Similar corrections were small to negligible for % lipid mixing of any samples with significant binding.

Example 5

Fluorescence Microscopy 25 nmole N-C12-DOPE/DOPC (70:30) liposomes, encapsulating TMR-70 kD dextran or labeled with NBD/Rh, and $5 \times 10^8$ erythrocyte ghosts were incubated at 37° C. for 30 minutes, with, or without, 1.25 mM $Ca^{2+}/Mg^{2+}$. At the end of the incubation period, ice cold 10 mM TES buffered saline with, or without, $Ca^{2+}/Mg^{2+}$ was added to each sample to bring the volume to 1 ml. The sample was centrifuged for 5 minutes at 3500xg, and the resulting pellet was washed once with the same buffer to remove unbound liposomes. The pellet was then resuspended in the same buffer and examined under an Olympus BH-2 fluorescence microscope (Olympus Corp., Lake Success, N.Y.), equipped with a 545 nm excitation filter (Olympus Corp.) and a >580 nm dichroic mirror (Olympus Corp.).

Example 6 pH-Dependence of Binding and Mixing to Erythrocyte Ghosts

Erythrocyte ghosts, prepared in accordance with the procedures described above, were incubated at 37 deg. C., for 1 hour in either a pH 7.4 or pH 4.9 medium and in the absence of divalent cation, with N-C12-DOPE/DOPC (70:30) liposomes, prepared in accordance with the procedures described above. The extents of liposome binding and lipid mixing was then determined, in accordance with the procedures described above.

Results of these experiments are presented in FIG. 8.

REFERENCES

Akoka, S., Tellier, C., Le Roux, C., & Marion, D. (1988) *Chem. Phys. Lipids* 46, 43–50.

Alpuche-Aranda, C. M., Swanson, J. A., Loomis, W. P., & Miller, S. I. (1992) *Proc. Natl. Acad. Sci. USA* 89, 10079–10083.

Bartlett, G. R. (1959) *J. Biol. Chem.* 234, 466–468.

Bertling W. M., Gareis, M., Paspaleeva, V., Zimmer, A., Kreuter, J., Nürnberg, E., & Harrer, P. (1991) *Biotech. Appl. Biochem.* 13, 390–405.

Bentz, J. (1993) *Viral Fusion Mechanisms.* CRC Press, Boca Raton, Fla.

Bomstein, R. A. (1965) *Biochem. Biophys. Res. Commun.* 21, 49–54.

Chernomordik, L. V., Kozlov, M. M., Melikyan, G. B., Abidor, I. G., Markin, V. S., & Yu, A. (1985) *Biochim. Biophys. Acta* 812,643–655.

Chu, C. J., Dijkstra, J., Lai, M. Z., Hong, K. and Szoka, F. C. (1990) *Pharm. Res.* 7, 824–34.

Clague, M. J., Schoch, C., Zech, L., & Blumenthal, R (1990) *Biochemistry* 29, 1303–1309.

Clarke, N. G., Hazlewood, G. P., & Dawson, R. M. C. (1976) *Chem. Phys. Lipids* 17, 222–232.

Connor, J. and Huang, L. (1985) *J. Cell Biol.* 101, 582–589.

Cullis, P. R., & de Kruijff, B. (1979) *Biochim. Biophys. Acta* 559, 399–420.

Dawson, R. M. C., Clarke, N., & Quarles, R. H. (1969) *Biochem. J.* 114, 265–270.

Domingo, J. C., Mora, M., & De Madariaga, M. A. (1993) *Biochim. Biophys. Acta* 1148, 308–316.

Düzgünes, N., & Papahadjopoulos, D. (1983) in *Membrane Fluidity in Biology: General Principles* (Aloia, R. C., Ed.) Vol 2. pp 187–216, Academic Press, NY.

Ellens, H., Siegel, D. P., Alford, A., Yeagle, P. L., Boni, L., Lis, L. J., Quinn, P., & Bentz, J. (1989) *Biochemistry* 28, 3692–3703.

Ellingson, J. S. (1980) *Biochemistry* 19, 6176–6182.

Epps, D. E., Schmid, P. C., Natarajan, V., & Schmid, H. O. (1979) *Biochem. Biophys. Res. Commun.* 90, 628–633.

Epps, D. E., Natarajan, V., Schmid, P. C., & Schmid, H. O. (1980) *Biochim. Biophys. Acta* 618, 420–430.

Fahey, D. A., & Small, D. M. (1986) *Biochemistry* 25, 4468–4472.

Feigenson, G. W. (1986) *Biochemistry* 25, 5819–5825.

Ganley, O. H., Graessle, O. E., & Robinson, H. J. (1958) *J. Lab. Clin. Med.* 51, 709–714.

Gething, M. J., Doms, R. W., York, D., & White, J. (1986) *J. Cell Biol.* 102, 11–23.

Gray, G. M., & Yardley, H. J. (1975) *J. Lipid Res.* 16, 441–447.

Gruner, S. M. (1985) *Proc. Natl. Acad. Sci. USA* 82, 3665–3669.

Hargin, K. D., & Morrison, W. R. (1980) *J. Sci. Food Agric.* 31, 877–888.

Hazlewood, G. P., & Dawson, R. M. C. (1975) *Biochem. J.* 150, 521–525.

Kuehl, Jr., F. A., Jacob, T. A., Ganley, O. H., Ormond, R. E., & Meisinger, M. A. P. (1957) *J. Am. Chem. Soc.* 79, 5577–5578.

Lafrance, D., Marion, D., & Pezolet, M. (1990) *Biochemistry* 29, 4592–2599.

Lee, K., Hong, K., & Papahadjopoulos, D. (1992) *Biochim. Biophys. Acta* 1103, 185–197.

Lee, K., Nir, S., & Papahadjopoulos, D. (1993) *Biochemistry* 32, 889–899.

Lee, Y., Zheng, Y. O., Taraschi, T. F., & Janes, N. (1996) *Biochemistry* 35, 3677–3684.

Litzinger, D. C., & Huang, L. (1992) *Biochim. Biochem. Acta* 1113, 201–227.

MacMurray, T. A., & Morrison, W. R. (1970) *J. Sci. Food Agric.* 21, 520–528.

Matsumoto, M., & Miwa, M. (1973) *Biochim. Biophys. Acta* 296, 350–364.

Mayer, L. D., Hope, M. J., & Cullis, P. R. (1986) *Biochim. Biophys. Acta* 858, 161–168.

Mercadal, M., Domingo, J. C., Bermudez, M., Mora, M., & De Madariaga, M. A. (1995) *Biochim. Biophys. Acta* 1235,281–288.

Morrison, W. R., Mann, D. L., Wong, S., & Coventry, A. M. (1975) *J. Sci. Food Agric.* 26, 507–521.

Natarajan, V., Reddy, P. V., Schmid, P. C., & Schmid, H. H. O. (1982) *Biochem. Biophys. Acta* 712, 342–355.

Natarajan, V., Schmid, P. C., Schmid, H. H. O., Reddy, P. V., & Zuzarte-Augustin, M. L. (1985) *Biochim. Biophys. Acta* 835, 426–433.

Newman, J. L., Stiers, D. L., Anderson, W. H., & Schmid, H. H. O. (1986) *Chem. Phys. Lipids* 42, 249–260.

Papahadjopoulos, D., Portis, A., & Pangborn, W. (1978) *Ann. N. Y. Acad. Sci.* 308, 50–63.

Papahadjopoulos, D., Nir, S., & Düzgünes, N. (1990) *J. Bioenerg. Biomemb.* 22, 157–179.

Parker, J. L., Claesson, P. M. & Attard, P. (1994) *J. Phys. Chem.* 98, 8468–8480.

Portis, A., Newton, C., Pangborn, W., & Papahadjopoulos, D. (1979) *Biochemistry* 18, 780–790.

Rand, R. P., & Sengupta, S. (1972) *Biochim. Biophys. Acta* 255, 484–492.

Reddy, P. V., Schmid, P. C., Natarajan, V., Muramatsu, T., & Schmid, H. H. O. (1984) *Biochim. Biophys. Acta* 795, 130–136.

Sato, S. B., Kawasaki, K., & Ohnishi, S. I. (1983) *Proc. Natl. Acad. Sci. USA* 80, 3153–3157.

Schmid, P. C., Reddy, P. V., Natarajan, V., & Schmid, H. H. O. (1983) *J. Biol. Chem.* 258, 9302–9306.

Schmid, H. H. O., Schmid, P. C., & Natarajan, V. (1990) *Prog. Lipid Res.* 29, 1–43.

Seddon, J. M., Kaye, R. D., Marsh, D. (1983) *Biochim. Biophys. Acta* 734, 347–352.

Siegel, D. P. (1993) *Biophys. J.* 65, 2124–2140.

Somerharju, P., & Renkonen, O. (1979) *Biochim. Biophys. Acta* 573, 83–89.

Stamatatos, L., Leventis, R., Zuckermann, M. J. and Silvius, J. R. (1988) *Biochemistry* 27, 3917–3925.

Steck, T. L. & Kant, J. A. (1974) *Methods Enzymol.* 31, 172–180.

Stegmann, T., White, J. M., & Helenius, A. (1990) *EMBO J.* 13, 4231–4241.

Straubinger, R. M., Duzgunes, N. and Papahadjopoulos, D. (1985) *FEBS Lett.* 179, 148–153.

Struck, D. K., Hoekstra, D., & Pagano, R. E. (1981) *Biochemistry* 20, 4093–4099.

Tanaka, Y., & Schroit, A. J. (1983) *J. Biol. Chem.* 258, 11335–11343.

Verkleij, A. J., Zwal, R. F. A., Roelofsen, B., Comfurius, P., Kastelijn, D., & Van Deenen, L. L. M. (1973) *Biochim. Biophys. Acta* 323, 178–193.

Verkleij, A. J. (1984) *Biochim. Biophys. Acta* 799, 43–63.

White, J. M., Kartenbeck, J., & Helenius, A. (1982) *EMBO J.* 1, 217–222.

Williamson, P., Algarin, L., Bateman, J., Choe, H. R., & Schlegel, R. A. (1985) *J. Cell Physiol.* 123, 209–214.

Wilson, M. J., Richter-Lowney, K., & Daleke, D. L. (1993) *Biochemistry* 32, 11302–11310.

Zhu, N., Liggitt, D., Liu, Y., & Debs, R. (1993) *Science* 261, 209–211.

What is claimed is:

1. A pharmaceutical composition comprising:

(a) a pharmaceutically acceptable carrier; and (b) a liposome having a lipid component which comprises:

(i) an N-acyl phosphatidylethanolamine (NAPE) having the formula:

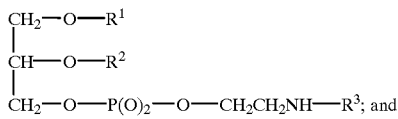

(ii) an additional lipid, wherein:

each of $R^1$, $R^2$ and $R^3$ is independently a group having the formula $-C(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$;

n1 is zero or an integer equal to from 1 to 22;

n3 is zero organ integer equal to from 1 to 19;

n5 is zero or an integer equal to from 1 to 16;

n7 is zero or an integer equal to from 1 to 13;

n9 is zero or an integer equal to from 1 to 10;

for each of $R^1$ and $R^2$ independently the sum of n1+2n2+n3+2n4+n5+2n6+n7+2n8+n9 is an integer equal to from 12 to 22, at least one of n2, n4, n6 and n8 is equal to 1;

for $R^3$ the sum of n1+2n2+n3+2n4+n5+2n6+n7+2n8+n9 is an integer equal to from 2 to 22;

each of n2, n4, n6 and n8 is independently equal to 0 or 1;

the lipid component comprises a destabilization-effective amount of the N-acyl phosphatidylethanolamine of from about 25 mole % to about 90 mole %; wherein the liposome is multilamellar or is a large unilamellar liposome wherein the destabilization-effective amount of the NAPE is that amount of NAPE which renders the liposome fusogenic when the liposome is admixed with a target, in the presence of divalent cations or at a pH of about 4.9 to about 6.0.

2. The pharmaceutical composition of claim 1, wherein for one or more of $R^1$ and $R^2$ at least one of n2, n4, n6 or n8 is equal to 1.

3. The pharmaceutical composition of claim 2, wherein for both of $R^1$ and $R^2$ at least one of n2, n4, n6 or n8 is equal to 1.

4. The pharmaceutical composition of claim 3, wherein each of $R^1$ and $R^2$ is $-C(O)(CH_2)_7(CH=CH)(CH_2)_7CH_3$.

5. The pharmaceutical composition of claim 1, wherein $R^3$ is $-C(O)(CH_2)_4CH_3$, $-C(O)(CH_2)_{10}CH_3$ or $-C(O)(CH_2)_{14}CH_3$.

6. The pharmaceutical composition of claim 5, wherein $R^3$ is $-C(O)(CH_2)_{10}CH_3$.

7. The pharmaceutical composition of claim 1, wherein the N-acyl phosphatidylethanolamine is

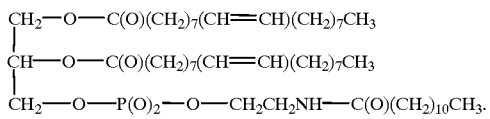

8. The pharmaceutical composition of claim 1, wherein the N-acyl phosphatidylethanolamine of the liposome comprises from about 25 mole % to about 80 mole % of the lipid component.

9. The pharmaceutical composition of claim 8, wherein the N-acyl phosphatidylethanolamine of the liposome comprises about 70 mole % of the lipid component.

10. The pharmaceutical composition of claim 1, wherein the additional lipid of the liposome is a phospholipid.

11. The pharmaceutical composition of claim 10, wherein the phospholipid is a phosphatidylcholine.

12. The pharmaceutical composition of claim 11, wherein the phosphatidylcholine is dioleoyl phosphatidylcholine.

13. The pharmaceutical composition of claim 1 wherein the lipid component of the liposome comprises N-dodecanoyl phosphatidylethanolamine and dioleoyl phosphatidylcholine.

14. The pharmaceutical composition of claim 13, wherein the N-dodecanoyl phosphatidylethanolamine comprises about 70 mole % of the liposome's lipid component and dioleoyl phosphatidylcholine comprises about 30 mole % of the lipid component.

15. The pharmaceutical composition of claim 1, wherein the additional lipid of the liposome is a phosphatidylethanolamine.

16. The pharmaceutical composition of claim 15, wherein the phosphatidylethanolamine is selected from the group consisting of trans-esterified phosphatidylethanolamine, dipalmitoyl phosphatidylethanolamine, palmitoyl oleoyl phosphatidylethanolamine and dioleoyl phosphatidylethanolamine.

17. The pharmaceutical composition of claim 15, wherein the phosphatidylethanolamine is a phosphatidylethanolamine conjugated to a moiety selected from the group consisting of dicarboxylic acids, polyethylene glycols, polyalkyl ethers and gangliosides.

18. The pharmaceutical composition of claim 1 wherein the liposome further comprises a targeting moiety selected from the group consisting of antibodies, cell receptor ligands and lectins.

19. The pharmaceutical composition of claim 1 wherein the liposome further comprises a bioactive agent selected from the group consisting of antiviral agents, antibacterial agents, antifungal agents, antineoplastic agents, antiinflammatory agents, radiolabels, radiopaque compounds, fluorescent compounds, mydriatic compounds, bronchodilators, local anesthetics, nucleic acid sequences and bioactive lipids.

20. A method of delivering a bioactive agent to a target which comprises contacting the target with a composition, wherein the composition comprises:

(a) a liposome having a lipid component which comprises:

(i) an N-acyl phosphatidylethanolamine (NAPE) having the formula:

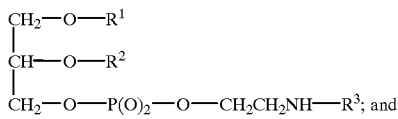

an additional lipid,
wherein;
each of $R^1$, $R^2$ and $R^3$ is independently a group having the formula $-C(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$;

n1 is zero or an integer equal to from 1 to 22;
n3 is zero or an integer equal to from 1 to 19;
n5 is zero or an integer equal to from 1 to 16;
n7 is zero or an integer equal to from 1 to 13;
n9 is zero or an integer equal to from 1 to 10;
for each of $R^1$ and $R^2$ independently the sum of n1+2n2+n3+2n4+n5+2n6+n7+2n8+n9 is an integer equal to from 12 to 22, at least one of n2, n4, n6 and n8 is equal to 1;
for $R^3$ the sum of n1+2n2+n3+2n4+n5+2n6+n7+2n8+n9 is an integer equal to from 2 to 22;
each of n2, n4, n 6 and n8 is independently equal to 0 or 1;
the lipid component comprises a destabilization-effective amount of the N-acyl phosphatidylethanolamine of from about 25 mole % to about 90 mole %; and wherein the liposome is multilamellar or is a large unilamellar liposome.

21. The method of claim 20, wherein the cell is a mammalian cell and the cell is contacted with the composition in the body of the mammal.

22. The method of claim 21, wherein the liposome additionally comprises a targeting moiety.

23. The method of claim 21, wherein the mammal is afflicted with a cancer and wherein the liposome comprises an anticancer effective amount of an anticancer agent.

24. The method of claim 20, wherein the target is a cell.

25. The method of claim 24, wherein the contacting is in vitro and wherein the contacting is in the presence of a physiological concentration of a cation or is at an acidic pH.

26. The method of claim 25, wherein the acidic pH is between pH about 4.9 to about 6.0.

27. The method of claim 24, wherein the cell is a nucleated cell, and the liposome is admixed with the nucleated cell at an acidic pH.

28. The method of claim 24, wherein the cell is a nucleated cell, and the liposome is admixed with the nucleated cell in the absence of added divalent cations.

29. The method of claim 27, wherein the acidic pH is between pH about 4.9 to about 6.0.

30. The method of claim 22, wherein the targeting moiety is selected from the group consisting of antibodies, cell receptor ligands and lectins.

31. The method of claim 20, wherein for one or more of $R^1$ and $R^2$ of the liposome at least one of n2, n4, n6 or n8 is equal to 1.

32. The method of claim 31, wherein for both of $R^1$ and $R^2$ at least one of n2, n4, n6 or n8 is equal to 1.

33. The method of claim 32, wherein each of $R^1$ and $R^2$ is $-C(O)(CH_2)_7(CH=CH)(CH_2)_7CH_3$.

34. The method of claim 26, wherein $R^3$ of the liposome is $-C(O)(CH_2)_4CH_3$, $-C(O)(CH_2)_{10}CH_3$ or $-C(O)(CH_2)_{14}CH_3$.

35. The method of claim 34, wherein $R^3$ is $-C(O)(CH_2)_{10}CH_3$.

36. The method of claim 20, wherein the N-acyl phosphatidylethanolamine is

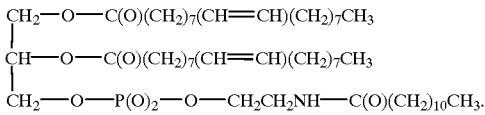

37. The method of claim 20, wherein the N-acyl phosphatidylethanolamine comprises from about 10 mole % to about 90 mole % of the lipid component.

38. The method of claim 37, wherein the N-acyl phosphatidylethanolamine comprises from about 20 mole % to about 80 mole % of the lipid component.

39. The method of claim 38, wherein the N-acyl phosphatidylethanolamine comprises about 70 mole % of the lipid component.

40. The method of claim 20, wherein the additional lipid is a phospholipid.

41. The method of claim 40, wherein the phospholipid is a phosphatidylcholine.

42. The method of claim 41, wherein the phosphatidylcholine is dioleoyl phosphatidylcholine.

43. The method of claim 20, wherein the liposome has a lipid component comprising N-dodecanoyl phosphatidylethanolamine and dioleoyl phosphatidylcholine.

44. The method of claim 42, wherein N-dodecanoyl phosphatidylethanolamine comprises about 70 mole % of the liposome's lipid component and dioleoyl phosphatidylcholine comprises about 30 mole % of the lipid component.

45. The method of claim 20, wherein the additional lipid is a phosphatidylethanolamine.

46. The method of claim 44, wherein the phosphatidylethanolamine is selected from the group consisting of trans-esterified phosphatidylethanolamine, dipalmitoyl phosphatidylethanolamine, palmitoyl oleoyl phosphatidylethanolamine and dioleoyl phosphatidylethanolamine.

47. The method of claim 44, wherein the phosphatidylethanolamine is a phosphatidylethanolamine conjugated to a moiety selected from the group consisting of dicarboxylic acids, polyethylene glycols, polyalkyl ethers and gangliosides.

48. The method of claim 20 wherein the liposome comprises a targeting moiety selected from the group consisting of antibodies, cell receptor ligands and lectins.

49. The method of claim 20, wherein the liposome comprises a bioactive agent selected from the group consisting of antiviral agents, antibacterial agents, antifungal agents, antineoplastic agents, antiinflammatory agents, radiolabels, radiopaque compounds, fluorescent compounds, mydriatic compounds, bronchodilators, local anesthetics, nucleic acid sequences and bioactive lipids.

50. The pharmaceutical composition of claim 1, wherein the divalent cations are employed at physiological concentrations.

51. The pharmaceutical composition of claim 1, wherein the target is a nucleated cell, and the liposome is admixed with the nucleated cell in the absence of added divalent cations.

* * * * *